(12) United States Patent
Neipel et al.

(10) Patent No.: US 6,174,685 B1
(45) Date of Patent: Jan. 16, 2001

(54) HUMAN HERPESVIRUS TYPE 6 PROTEIN P100, THE CORRESPONDING DNA SEQUENCES, THEIR PREPARATION AND USE

(75) Inventors: Frank Neipel, Erlangen; Bernhard Fleckenstein, Wiesenthau, both of (DE)

(73) Assignee: Behring Diagnostics GmbH, Marburg (DE)

( * ) Notice: Under 35 U.S.C. 154(b), the term of this patent shall be extended for 0 days.

(21) Appl. No.: 08/467,528

(22) Filed: Jun. 6, 1995

Related U.S. Application Data

(62) Division of application No. 08/266,311, filed on Jun. 27, 1994, which is a continuation of application No. 08/126,435, filed on Sep. 24, 1993, now abandoned, which is a continuation of application No. 07/908,041, filed on Jul. 6, 1992, now abandoned.

(30) Foreign Application Priority Data

Jul. 8, 1991 (EP) .................................................. 91111338

(51) Int. Cl.⁷ .................................................. G01N 33/53
(52) U.S. Cl. ........................ 435/7.1; 435/7.92; 530/350; 530/389.4
(58) Field of Search ................................ 435/172.3, 69.1, 435/69.7, 7.1, 7.92; 530/389.4, 350; 424/186.1

(56) References Cited

PUBLICATIONS

Littler et al., Identification, Cloning, and Expression of the Major Capsid Protein Gene of Human Herpesvirus 6, Journal of Virology, vol. 64, No. 2, Feb. 1990, p. 714–772.

Larcher et al., Serological Crossreaction of Human Herpesvirus 6 with Cytomegalovirus, The Lancet, Oct. 22, 1988, p. 963–964.

Neipel et al., The Unique Region of the Human Herpesvirus 6 Genome is Essentially Collinear With the $U_L$ Segment of Human Cytomegalovirus, Journal of General Virology (1991), 72, p. 2293–3397.

Chang et al., Identification, Characterization, and Sequence Analysis of a cDNA Encoding a Phosphoprotein of Human Herpesvirus 6, Journal of Virology, vol. 65, No. 6, Jun. 1991, p. 288–2894.

Lawrence et al., Human Herpesvirus 6 Is Closely Related to Human Cytomegalovirus, Journal of Virology, vol. 64, No. 1, Jan. 1990, p. 287–299.

Josephs et al., Genomic Analysis of the Human B–Lymphotropic Virus (HBLV), Science, vol. 234, (Oct. 31, 1986), pp. 601–603.

Neipel et al., Gene for the Major Antigenic Structural Protein (p100) of Human Herpesvirus 6, The Journal of Virology, vol. 66, No. 6, (Jun. 1992), pp. 3918–3924.

Yamamoto et al., Identification of a Nucleocapsid Protein as a Specific Serological Marker of Human Herpesvirus 6 Infection, Journal of Clinical Microbiology, vol. 28, No. 9, Sep. 1990, p. 1957–1962.

*Primary Examiner*—James Ketter
*Assistant Examiner*—Irem Yucel
(74) *Attorney, Agent, or Firm*—Finnegan, Henderson, Farabow, Garrett & Dunner, L.L.P.

(57) ABSTRACT

The invention relates to the human herpesvirus type 6 protein p100 and parts thereof having its specific immunological properties. It further relates to antibodies directed to them and to the corresponding DNA sequences. They can be used in pharmaceutical or diagnostic compositions, optionally together with other HHV-6 proteins or the corresponding DNA sequences.

6 Claims, 11 Drawing Sheets

SEQUENCES OF THE VIRAL INSERTS OF CLONES pMF94 AND pMF295.
BOTH SEQUENCES ARE PART OF THE MAJOR CAPSID PROTEIN GENE
OF HHV-6 AS PUBLISHED IN (LITTLER ET AL. 1990).

NUCLEOTIDE SEQUENCE OF pMF94

```
  1 GAATTCCTGA CGCCAGCGCC ACAGGCCTTG TTATTTGATA GTGCCGGGAG
 51 TACGCAGAAG TAAAATATCT TGCTCAGGAT GGTGGTTTCG TTCGATGGTC
101 TGTCATTGTC GGTAAAGACG ACGCTTGAAT CTATTAGATT CATTCTTTGC
151 ACATCGGATA TTTCGTAATT TCTAACTCTT ACGGTGTTCT GTGTCAGTGG
201 TGTATCATCC GCTGTTATTT TTGCATTCGT GTCGTTTCTG GGCATGGTAT
251 GGACGAACGG GCAGAACAGA CGTCCGTCGA ACAACGCGTT GGCGAAATTC
301 ACCAGAGGTT CGCCGCAAAG TTGCTCGTTG AGGTTGGAGA TAGAGATTGT
351 TCTCTTCACT AGGCGAATTA GCGACACAAG ATTTCTGTAG TGAGCGAAAG
401 CTGCTCCCGG GATCAGTTCG TCGCCCATGT GGTTGGAATT C (SEQ ID NO: 5)
```

NUCLEOTIDE SEQUENCE OF pMF295

```
  1 CCGTGTGAAA TTAAACGACA CCATGGAAAA CAACCTACCC ACCAGCGTTT
 51 TTTTCCACAA TAAAGACCAA GTCGTGCAGC GAATTGATTT TGCCGACATA
101 TTACCGTCGG TTTGCCATCC CATTGTCCAC GACTCGACCA TCGTCGAACG
151 ACTCATGAAA AGCGAACCAT TGCCTACCGG CCACCGCTTT TCCCAACTAT
201 GTCAACTAAA AATTACCCG (SEQ ID NO:6)
```

FIG. 1

SEQUENCE OF THE VIRAL INSERT OF CLONE pMF90. THE
SEQUENCE IS IDENTICAL WITH NUCLEOTIDES 117-194 OF THE
SEQUENCE PUBLISHED IN (CHANG AND BALACHANDRAN, 1991).

```
  1       CCA CTTTTTGAAA GTTTTATGAA CATCATCTCG AATCCTGAGG
 51   TTACGAAGAT GTACATTCAG CATGATAGTG ATCTGTATAC GAGGGTTTTG
101   GTAACGGCTT CCGATACATG TACACAGGCG TCGGTTCCCT GTGTGCACGG
151   ACAAGAAGTG GTGCGAGACA CCGGGAGATC GCCGTTGAGG ATTGACCTTG
201   ATCATTCGAC CG (SEQ ID NO:7)
```

FIG. 2

COMPLETE SEQUENCE OF THE HHV-6 EcoRI FRAGMENTS NUMBERED 6 AND 7 (STARTING FROM THE LEFT END). THESE FRAGMENTS CONTAIN THE ENTIRE p100 GENE OF HHV-6. THE POSITION OF pROS EXPRESSION CLONES IS INDICATED WITHIN THE SEQUENCE.

```
E
c
o
R
I
  GAATTCCTATGTTNCGCCCCGTGCTAGATGTTTTACTTTCAGTCTTTTTACGCCGGTGTAAGGTTTTGTACC
1------------------------------------------------------------------------72
  TGATAGTTGCGATTATAGCTAGCATGCTTATACTATATGAACAGACTGCATGATAGATGAAGTAAACTAACT
73-----------------------------------------------------------------------144
  GACAGAAAAAACGGTTGAATGAGAACAGTTGCTTTCTGTTCACTGTCATAAAAAAGACACACCACATGAGCA
145----------------------------------------------------------------------216
  CAAAATCGCTAGCAAAGAGTGTGATGACGTAAAATGAAGTAGCGTTATGTTTTGCGACTCTGTGGTAGAGAA
217----------------------------------------------------------------------288
  TCATGGTGGTAACCACTATAATGATCATGGGGATAGATGTGGTGAGCGTGATTCCGGTAACTGCGCTCTCCA
289----------------------------------------------------------------------360
  TGATTCGTGCTGTCTTTAGCGTGGGTGTCGAGGTACAGGAAGCATTGCCTTTGAACTCTTCATTGCGCTATT
361----------------------------------------------------------------------432
  AAAGATATTGAATGTTATTTTCATGTTACGCTACATTAAAATATTCGGTAACAATGATGTCTGAAGACTTAC
433----------------------------------------------------------------------504
  CAGAAGTTTGGACAGCTCAATGACAGTGTCCATCTCGTCGCTTGTCAGTTTTCTGTGTGGGTAAAAAAAAGA
505----------------------------------------------------------------------576
  CTATTAAACATTGAATGTTGGCGGAAATGAGCAGTTCTGTTTTTGAGTTTGTTTTCTAAAATATGGATCTGC
577----------------------------------------------------------------------648
                                                               M  D  L  Q-
  AAAGACATCCGATTCCGTTTGCGTGGCTAGATCGAGACAAAGTTGAGCGTCTTACAGATTTTCTCAGCAATT
649----------------------------------------------------------------------720
   R  H  P  I  P  F  A  W  L  D  R  D  K  V  E  R  L  T  D  F  L  S  N  L-
  TGGAAAGACTGGATAATGTAGATTTGCGAGAGcaTCCCCATGTGACTAATTCTTGTGTCGTGAGAGAGGGAG
```

FIG. 3-1

```
722----------------------------------------------------------------------792
     E  R  L  D  N  V  D  L  R  E  H  P  H  V  T  N  S  C  V  V  R  E  G  D-
                 D
                 r  ----BEGIN OF pDF446-4
                 a
                 I
     ACGATGTAGACGATTTAAAAACATTGTATAACCTACTAGTGTTATGGCTTATGTATCACTACGTCTTATCTA
793----------------------------------------------------------------------864
     D  V  D  D  L  K  T  L  Y  N  L  L  V  L  W  L  M  Y  H  Y  V  L  S  K-
     AAAGGAAGCCGGATTATAATGCTATATGGCAAGACATCACGAAACTCCAAAGTGTCGTAAACGAGTACTTAA
865----------------------------------------------------------------------936
     R  K  P  D  Y  N  A  I  W  Q  D  I  T  K  L  Q  S  V  V  N  E  Y  L  N-
     ACTCCAAGGTCTGAATAAAGGAATTTTTGAAAAATATGTTCACGAACAAAGAAAAGTTTGAATCGCAATTCA
937---------------------------------------------------------------------1008
     S  K  G  L  N  K  G  I  F  E  N  M  F  T  N  K  E  K  F  E  S  Q  F  S-
     GTGATATTAATCGCGCTTTACTGCGTTTAGGAAACTTTATTAAGTGGGGTAGCAATGTTGCGATCGATACTC
1009--------------------------------------------------------------------1080
     D  I  N  R  A  L  L  R  L  G  N  F  I  K  W  G  S  N  V  A  I  D  T  P-
     CTTATGTAAATCTTACTGCAGAAGACAGCAGCGAGATAGAAAATAATTTGCAAGATGCTGAAAAAAACATGC
1081--------------------------------------------------------------------1152
     Y  V  N  L  T  A  E  D  S  S  E  I  E  N  N  L  Q  D  A  E  K  N  M  L-
     TGTGGTATACCGTCTATAACATAAATGACCCCTGGGACGAAAACGGTTACTTAATAACGAGTATTAATAAAT
1153--------------------------------------------------------------------1224
     W  Y  T  V  Y  N  I  N  D  P  W  D  E  N  G  Y  L  I  T  S  I  N  K  L-
     TAATTTATCTCGGTAAGTTATTTTTAGCGTTAACTCAGTCCTGGTCAAAGCTAGAAAAGGTTGCTATGAGTC
1225--------------------------------------------------------------------1296
     I  Y  L  G  K  L  F  L  A  L  T  Q  S  W  S  K  L  E  K  V  A  M  S  Q-
     AAATTGTAATCACGCAAAATCATCTCTCGGGTCATTTGAGGAGGCACGACAATTTTAATATTGTATATTCTC
1297--------------------------------------------------------------------1363
     I  V  I  T  Q  N  H  L  S  G  H  L  R  R  H  D  N  F  N  I  V  Y  S  H-
     ATAGGGTTTTGCAGACTCCTCTGACTGGTCAAAGAGTAGAGAGTTTTCTGAAAATAATCACCAGTGATTATG
1369--------------------------------------------------------------------1440
     R  V  L  Q  T  P  L  T  G  Q  R  V  E  S  F  L  K  I  I  T  S  D  Y  D-
                                                                        H
                                                                        a
                                       END OF pDF446-4----- e -BEGIN
                                                            I  OF
                                                            I  pD2Hae
                                                            I
     ATATTATCAAAAGTAGTCTGGAATCACACAGCGCGTCGAAAGCATTTTCGATGTCTGAGATTGGGCCTAATT
1441--------------------------------------------------------------------1512
```

FIG. 3-2

```
       I  I  K  S  S  L  E  S  H  S  A  S  K  A  F  S  M  S  E  I  G  P  N  S-
     CTTTAATGGATTTCGTCCCTTTACGCGGCGATATACATTCAAATTTGACTTTACCTAGTATGTCTATAGATA
1513------------------------------------------------------------------------1584
       L  M  D  F  V  P  L  R  G  D  I  H  S  N  L  T  L  P  S  M  S  I  D  T-
     CAAAGAAATCATCTTTAGATCCGGCTCGTCTGAAAAAAAGTAATTCCAGAAGTTTGGATAGTTTCTTAAGAA
1585------------------------------------------------------------------------1656
       K  K  S  S  L  D  P  A  R  L  K  K  S  N  S  R  S  L  D  S  F  L  R  M-
     TGCAGAGACAACCTAAATTTCTAGAGTTGGATAGCGTTGATAATGCCGGGGAAAAAATTTTACTAAAGGAAG
1657------------------------------------------------------------------------1728
       Q  R  Q  P  K  F  L  E  L  D  S  V  D  N  A  G  E  K  I  L  L  K  E  A-
     CAACACTCGGGGGTGAAAACGTTAAAGCGACAACGCCTGCTTCCTCTGTCTCTTTAATGTCCGGAGTTGAGT
1729------------------------------------------------------------------------1800
       T  L  G  G  E  N  V  K  A  T  T  P  A  S  S  V  S  L  M  S  G  V  E  S-
     CGCCGTCGTCTTTCACTTCTACCAATCTGGATCTGCCGTTGTCGTCTTTCACTTCTACTAATCTGGATCTGC
1801------------------------------------------------------------------------1872
       P  S  S  F  T  S  T  N  L  D  L  P  L  S  S  F  T  S  T  N  L  D  L  R-
                                       H
                                       a
           END OF pD2Hae -----          e    ------BEGIN OF pDF446-3
                                       I
                                       I
                                       I
     GAGATAAGTCGCACGGTAATTATAAAATTGGCCCTTCGGGGATTTTAGATTTTAATGTTAAATTTCCACCTA
1873------------------------------------------------------------------------1944
       D  K  S  H  G  N  Y  K  I  G  P  S  G  I  L  D  F  N  V  K  F  P  P  N-
     ATGCGCAATTGAATACGAACGGTGTGGATTTACTACAGGATAAAACTTCGATCGGGAGTCCCAGTAGCGGTA
1945------------------------------------------------------------------------2016
       A  Q  L  N  T  N  G  V  D  L  L  Q  D  K  T  S  I  G  S  P  S  S  G  I-
     TTACCGATGTGGTAAATGGTTTCGCTAATCTCAATCTGCATCAGAATAAATCAAATGTTTCGCCACCGTGGA
2017------------------------------------------------------------------------2088
       T  D  V  V  N  G  F  A  N  L  N  L  H  Q  N  K  S  N  V  S  P  P  W  S-
     GCAGAAACACAGCGGCGAATGCGGACTTTTTAGATCCGGTGCATCGCTTTGTTCCTGAGCAGACAGGGACAC
2089------------------------------------------------------------------------2160
       R  N  T  A  A  N  A  D  F  L  D  P  V  H  R  F  V  P  E  Q  T  G  T  P-
     CCTTCGTGTTGAATAATTCCGACGTGGCGGGATCAGAAGCGAAGCATACGACTTACAGTACGGAGACCGGCG
2161------------------------------------------------------------------------2232
       F  V  L  N  N  S  D  V  A  G  S  E  A  K  H  T  T  Y  S  T  E  T  G  V-
     TTTCACCCCGTAACGTTTTTCTCATTAAAGATTTGAGAGGCAAAGACGGTTTTAGGAAACAGAAGCAGTCAG
2233------------------------------------------------------------------------2304
       S  P  R  N  V  F  L  I  K  D  L  R  G  K  D  G  F  R  K  Q  K  Q  S  D-
     ATATTCCGAAAAGCTTAACTAAGGAAAGAAATGATAAAGCTATAATGCACTCACGCGAGGTGACCGGAGATT
2305------------------------------------------------------------------------2376
```

FIG. 3-3

```
           I  P  K  S  L  T  K  E  R  N  D  K  A  I  M  H  S  R  E  V  T  G  D  S-
                                      E
              END OF pDF446-3----  c  ---- BEGIN OF pD2Hind
                                      o
                                      R
                                      I
      CTGGCGATGCGACTGAAACTGTGGGTGCTCGGAATTCCCCGGCGTTGAGAAAAATTAAGCAAGCAAATGATT
2377--------------------------------------------------------------------2448
          G  D  A  T  E  T  V  G  A  R  N  S  P  A  L  R  K  I  K  Q  A  N  D  F-
      TTTTTGCCGGGTTAAATAAGAAAAATGATCGTGACGTATTAAGAGGGGGGAAAGGAAATAGCAAGGACTTGC
2449--------------------------------------------------------------------2520
          F  A  G  L  N  K  K  N  D  R  D  V  L  R  G  G  K  G  N  S  K  D  L  H-
      ATTCTGGCGGCAATGCAAAAAAAAAAGAAATGTCGGGAAAGTTTAATGACGATAAAGAAATGACGCGAAACG
2521--------------------------------------------------------------------2592
          S  G  G  N  A  K  K  K  E  M  S  G  K  F  N  D  D  K  E  M  T  R  N  G-
      GACAAGAGCCATCACGTAGTTTAATGGGAGATGCTAGAAATGCCGGAGATGAACAATATATTCAAGCGGGTC
2593--------------------------------------------------------------------2664
          Q  E  P  S  R  S  L  M  G  D  A  R  N  A  G  D  E  Q  Y  I  Q  A  G  L-
      TCGGGCAGCGAGTTAACAATCTTCTAAGTCAATTTACAAATCTGATTAGTTTAGGCGAGAAGGGCATCGAAG
2665--------------------------------------------------------------------2736
          G  Q  R  V  N  N  L  L  S  Q  F  T  N  L  I  S  L  G  E  K  G  I  E  D-
      ACATTTTGCAGAATCAGCGCGGGACCGAGTTAAAGTTGGCTACAGAAAACAAGTCGGGACGCGAATCGGAGG
2737--------------------------------------------------------------------2808
          I  L  Q  N  Q  R  G  T  E  L  K  L  A  T  E  N  K  S  G  R  E  S  E  E-
      AAGCTAACGTAGAAAAAATTCTTGAAGTTAGTAATCCTCAAGATATGTTTAAAAATTTTAGGTTGCAAAACG
2809--------------------------------------------------------------------2880
          A  N  V  E  K  I  L  E  V  S  N  P  Q  D  M  F  K  N  F  R  L  Q  N  D-
      ATCTCGATTCCGTTCAGTCTCCGTTTAGGCTACCGGATGCTGATTTGTCTCGCGAGTTAGATTCCGCGTCAT
2881--------------------------------------------------------------------2952
          L  D  S  V  Q  S  P  F  R  L  P  D  A  D  L  S  R  E  L  D  S  A  S  F-
                            H
         END OF pD2Hind -----  i
                               n
                 BEGIN      d
                OF pMF101R  I
                            I
                            I
      TTAAGGACGCGTTAGACTTGAAGCTTCCGGGTAACGGAGAACGAGAAATAGATCTCGCTCTTGAAAAAGTGA
2953--------------------------------------------------------------------3024
          K  D  A  L  D  L  K  L  P  G  N  G  E  R  E  I  D  L  A  L  E  K  V  K-
```

FIG. 3-4

```
          AGGTAGGCGAGACGGAAACCTCAGATTTAAAAGTCGGTCAGGATGAAAGTTTTGTTCCTGCGCAATTAATGA
    3025---------------------------------------------------------------------3096
             V  G  E  T  E  T  S  D  L  K  V  G  Q  D  E  S  F  V  P  A  Q  L  M  K-
                              END OF pMF101R ─────────┐
                                                      │
          AGGTTGAGACACCTGAAGAAAAAGATGATATAATTGAACAGATGGTTCTGAGGATACGTCAAGACGGGGAAA
    3097---------------------------------------------------------------------3168
             V  E  T  P  E  E  K  D  D  I  I  E  Q  M  V  L  R  I  R  Q  D  G  E  T-
          CTGATGAAAACACCGTCTCTGGGCCGGGAGTCGCTGAGTCTTTGGATATAGAAGCCAAAGGCGAGTCAGCGA
    3169---------------------------------------------------------------------3240
             D  E  N  T  V  S  G  P  G  V  A  E  S  L  D  I  E  A  K  G  E  S  A  I-
          TCGCGTCGTGATGTAAAAAATTTTCTCTGGGGAGTTTCAGGTTGCCAATAAAATGCCCATTCTCAGACAGCT
    3241---------------------------------------------------------------------3312
             A  S  *
          TTGCGATTACGTCTTTTTTGTTCATTGTTCTGGCTTGTCATTCTTTCTACATAAAACAGGGTCGCGATAGGTG
    3313---------------------------------------------------------------------3384
          TGCTTTGAGGCAGGATCAGATTTGGAGAAAATGAACGCAGCGTAATGTGCAAAGGTGTTCCCGGGGCCCACA
    3385---------------------------------------------------------------------3456
          GCATCACCTGGGTTTCGAAGAATCCTTCGTTCTGGTAGCCGGATATGAGGATTTGCTTGTCGGGCTTTGTGA
    3457---------------------------------------------------------------------3528
          AATATCGGATAGGTAGAATTACTATGTGGCATCGGCTTGGATAGAAATGGATGTCATATGGTGCGTGTACAA
    3529---------------------------------------------------------------------3600
          GTAGCTCGTAATAATTTGGGTTGTGTTGCAGTTGTATCGTTGCGTTTAGTACGTCTCCTGTAAAATATAATT
    3601---------------------------------------------------------------------3672
          TCGGGTTACTGGAAAATAACAGNGGTTCGGGCTCTTCGATTTGCGTTACCACTTCAAACTGAACTATTAAAT
    3673---------------------------------------------------------------------3744
          ATTTCGGTAGATTTTCCGTTGTTAGTAAAGAAGGGATTTGCTCGCAGCATACAGTGGCTAGTGTTCCAAAAA
    3745---------------------------------------------------------------------3816
                                                                              E
                                                                              c
                                                                              o
                                                                              R
                                                                              I
          CTTTTTCTTTGTTTTTGACGAGACCGAGATTTTCAATGTTAATCGAGAATTC (SEQ. ID NO:8)
    3817----------------------------------------------3868
```

FIG. 3-5

REACTIVITY OF HUMAN SERA WITH HHV-6 EPITOPES

1: pMF101R (HHV-6 p100, homol. TO HCMV pp 150)
2: pD2MF90, (PARTIALLY) CLEAVED WITH FXa; homol. TO HCMV UL44
3: pROS (NEGATIVE CONTROL)

HUMAN HERPESVIRUS TYPE 6 PROTEIN P100, THE CORRESPONDING DNA SEQUENCES, THEIR PREPARATION AND USE

This is a division of application Ser. No. 08/266,311, filed Jun. 27, 1994, which is a continuation application of Ser. No. 08/126,435, filed Sep. 24, 1993, now abandoned which is a continuation application of Ser. No. 07/908,041, filed Jul. 6, 1992, now abandoned.

The present invention relates to the human herpesvirus type 6 protein p100 and parts thereof having its specific immunological properties. It further relates to antibodies specifically reacting with the protein or parts thereof and to DNA sequences encoding said protein or parts thereof, to recombinant vectors containing these DNA sequences and to host organisms transformed with these vectors. Furthermore, it relates to the preparation of the proteins and DNA sequences and their use in pharmaceutical or diagnostic compositions.

The human herpesvirus type 6 (HHV-6) has recently been shown to be closely related to human cytomegalovirus (HCMV) on the basis of amino acid sequence homology (Littler et al., 1990; Lawrence et al., 1990; Chang and Balachandran, 1991; Neipel et al., 1991), genomic position and orientation of conserved herpesvirus genes (Neipel et al., 1991), and antigenic properties (Larcher et al., 1988; Yamamoto et al., 1990; Littler et al., 1990). Until today, only two proteins of HHV-6 and their genes have been described in more detail: the major capsid protein (MCP) (Littler et al., 1990) with a molecular weight of 135 kda, and a phosphoprotein of 41 kda termed HHV-6 p41 (Chang and Balachandran, 1991). The latter one is homologous to UL44 of HCMV.

In order to be able to distinguish infections caused by HHV6 and HCMV it is desirable to have a reagent which is specific for the human herpesvirus type 6.

Thus, the technical problem underlying the present invention essentially is to provide a protein having immunogenic properties and the capability to induce the formation of antibodies lacking crossreactivity with HCMV and other human herpesviruses. Furthermore, it is a technical problem to provide the corresponding DNA sequences.

The solution to this technical problem is achieved by providing the embodiments characterized in the claims.

The present invention therefore relates to a DNA sequence encoding the HHV-6 (human herpesvirus type 6) protein p100 having the amino acid sequence given in FIGS. 3A–3E (SEQ ID NO:1) starting from the position corresponding to nucleotide 639 to the position corresponding to nucleotide 3248.

The protein p100 is a structural protein from human herpesvirus type 6 with a molecular weight of about 100 kda that is in part homologous to pp150 of HCMV. It can be obtained by expression of the gene which is located in the region of the EcoRI fragments 6/7 of HHV-6 strain U1102 (distance to the left end of the HHV-6 genome 21–25 kb). The protein p100 has immunogenic properties and lacks crossreactivity with human cytomegalovirus and other human herpesviruses (Yamamoto et al., 1990). It can, therefore, be used as a reagent for detecting HHV-6 antibodies and for the differential diagnosis of HHV-6 infection versus CMV-infection.

The present invention further relates to the corresponding DNA sequence given in FIGS. 3A–3E (SEQ ID NO:2) from position 639 to position 3248.

A DNA sequence encoding p100 can be isolated from an HHV-6 genome as disclosed herein. If the obtained DNA sequence differs from the DNA sequence given in FIG. 3, the above DNA can be derived therefrom by conventional in vitro mutagenesis techniques. Furthermore, the person skilled in the art equipped with the technical teaching disclosed herein will be able to obtain the DNA sequences of the present invention by conventional DNA synthesis techniques.

In a further embodiment, the present invention relates to a DNA sequence hybridizing to the above DNA sequence and encoding a protein having the specific immunological properties of the HHV-6 protein p100. In this context, the term "hybridization" refers to conventional hybridization conditions, preferably to hybridization conditions under which the $T_m$ value is between $T_m=-20$ to $T_m=-27°$ C. Most preferably, the term "hybridization" refers to stringent hybridization conditions. The term "having the specific immunological properties" characterizes the entire protein defined by the amino acid sequence in FIG. 3 as well as parts of this protein which react with antibodies specific for the protein and substantially without crossreactivity to components of human cytomegalovirus and other herpesviruses. Examples of such immunogenic parts or epitopes of the protein are the amino acid sequences encoded by the nucleotide sequence given in FIG. 3 from position 2960 to position 3141 (SEQ ID NO:3) or the nucleotide sequence given in FIG. 3 from position 2408 to position 2959 (SEQ ID NO:4). These epitomes may also be used in the diagnostic composition described below.

The present invention further relates to recombinant vectors containing the above DNA sequences whereby the DNA sequences may be under the control of a homologous or heterologous promoter allowing its expression in a desired host cell.

A further embodiment of the present invention is a host organism transformed with one of the recombinant vectors of the present invention wherein the host organism is a bacterium, preferably of the genus Escherichia, a yeast, preferably of the genus Saccharomyces, a plant cell or an animal cell, preferably a mammalian cell.

The present invention also relates to the preparation of the HHV-6 protein p100 which comprises the steps of cultivating a transformed host organism and recovering said protein from the culture.

A further object of the present invention is to provide antibodies specifically reacting with the HHV-6 protein p100 or parts thereof having its specific immunological properties but not with components of human cytomegalovirus and other herpesviruses. The person skilled in the art provided with the proteins and fragments thereof of the present invention can produce these antibodies according to conventional methods. In a preferred embodiment of the antibodies of the present invention, the antibodies are monoclonal antibodies.

Another object of the invention is to provide pharmaceutical compositions containing the HHV-6 protein p100 or parts thereof having its specific immunological properties and/or antibodies directed to them, wherein the pharmaceutical compositions are suitable for the prophylaxis or treatment of HHV-6 infections.

A further object of the invention is to provide a composition containing the HHV-6 protein p100 or parts thereof having its specific immunological properties or the corresponding DNA sequences or antibodies of the invention.

These compositions may additionally contain parts of the major capsid protein gene of HHV-6, especially the DNA sequences given in FIG. 1 (SEQ ID NOS:5 and 6) and/or the polypeptide being encoded by these DNA sequences or parts of the gene encoding the phosphorylated HHV-6 protein of 41 kda, especially the DNA sequence given in FIG. 2 (SEQ ID NO:7) and/or the polypeptide being encoded by these DNA sequences. Since the HHV-6 protein p100 has the capability to induce the formation of antibodies lacking crossreactivity with human cytomegalovirus or human herpesviruses, it may be used in the differential diagnosis for distinguishing whether an infection is caused by HHV-6 or human cytomegalovirus or other herpesviruses.

The present invention is explained in more detail in the following description and the figures:

FIG. 1 shows the DNA sequences of the viral inserts of clones pMF94 (SEQ ID NO:5) and pMF295 (SEQ ID NO:6). Both sequences are part of the major capsid protein gene of HHV-6 as published in Littler et al., 1990.

FIG. 2 shows the DNA sequence of the viral insert of clone pMF90 (SEQ ID NO:7). The sequence is identical with nucleotides 117–194 of the sequence published in Chang and Balachandran, 1991.

FIGS. 3A–3E shows the complete DNA sequence of the HHV-6 EcoRI fragments numbered 6 and 7 (starting from the left end) (SEQ ID NO:8). These fragments contain the entire p100 gene of HHV-6. Furthermore, the amino acid sequence of p100 is shown.

Figure 4:
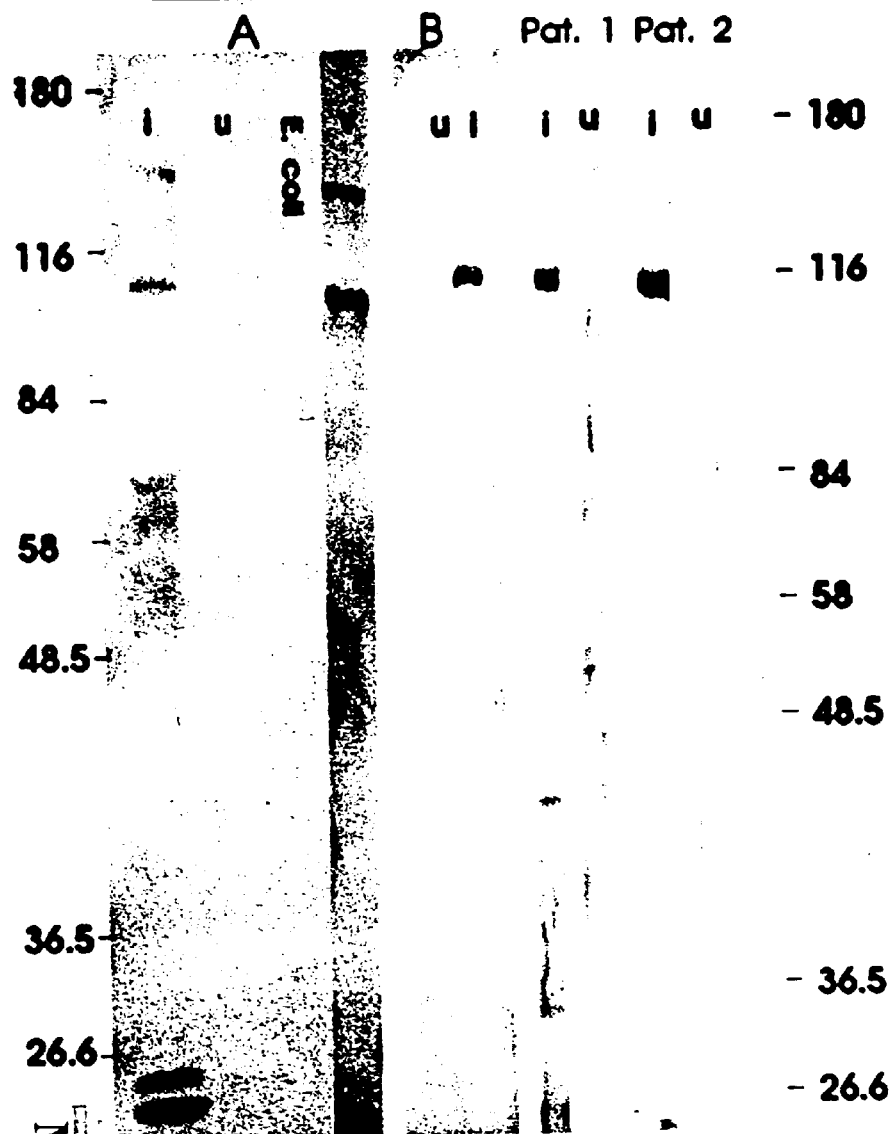

FIG. 4 shows a Western blot analysis wherein antiserum of rabbits immunized with HHV-6 infected HSB-2 cells and antibodies against the HHV-6 protein p100 purified from this antiserum are reacted with viral proteins.

Figure 5A:
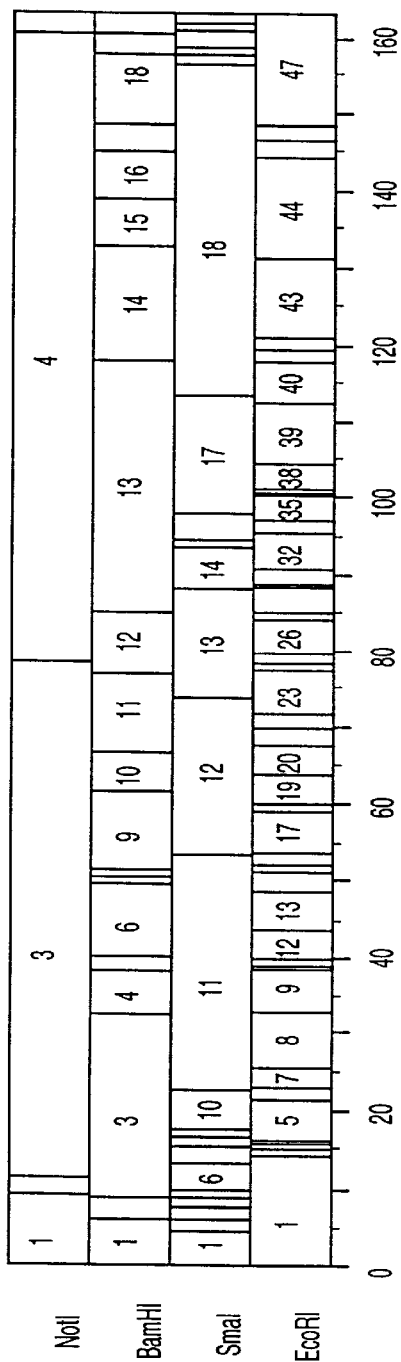
Figure 5B:
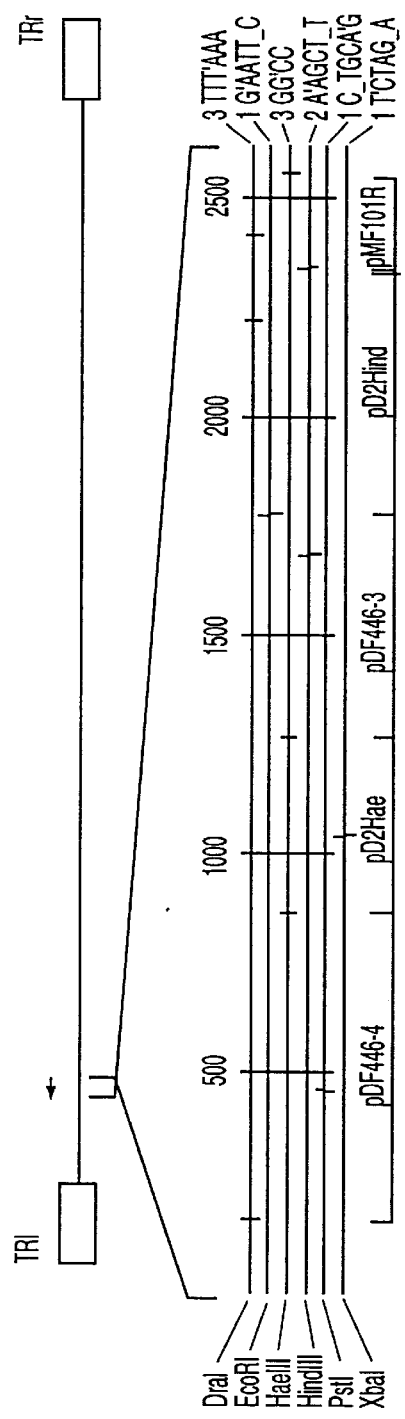

FIGS. 5A and 5B show the restriction map of the HHV-6 genome.

Figure 6:
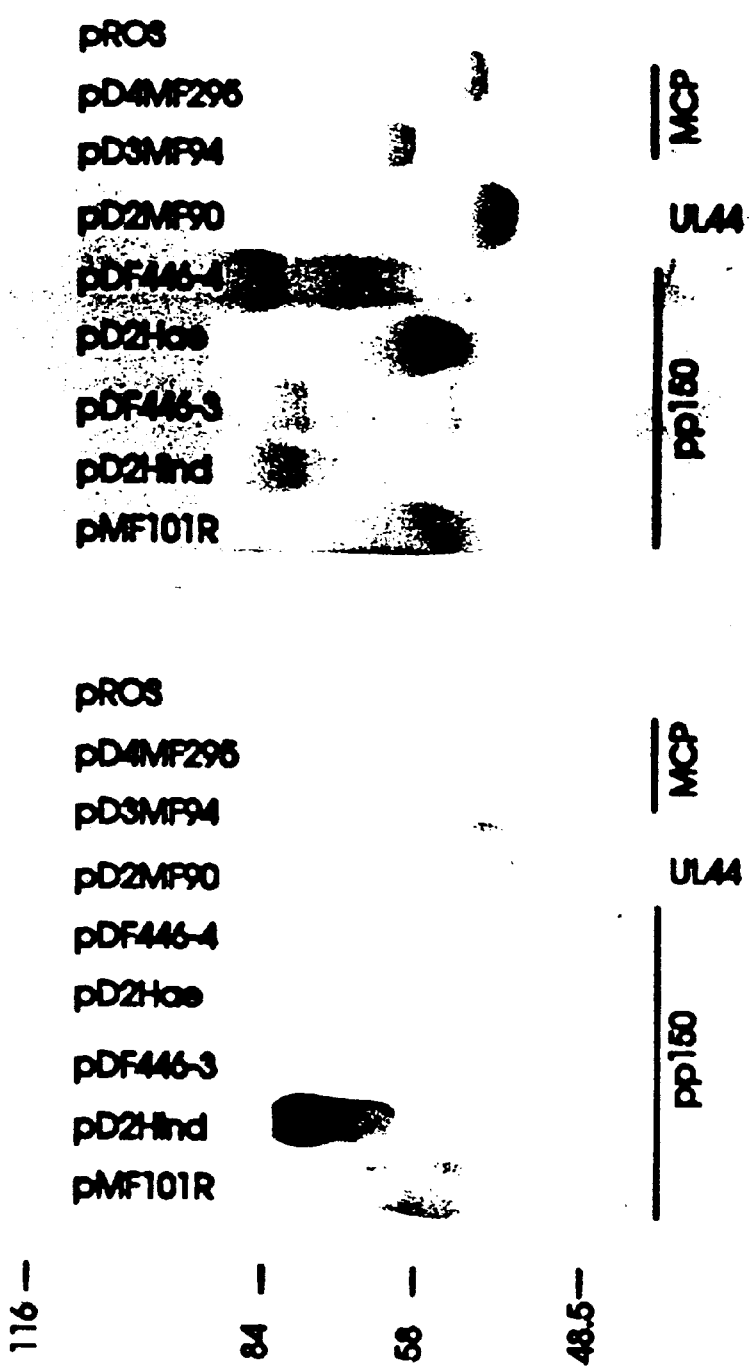

FIG. 6 shows the results of the expression of HHV-6 proteins in the expression vector pROS in a Western blot with rabbit serum and a PAGE Coomassie staining.

Figure 7:
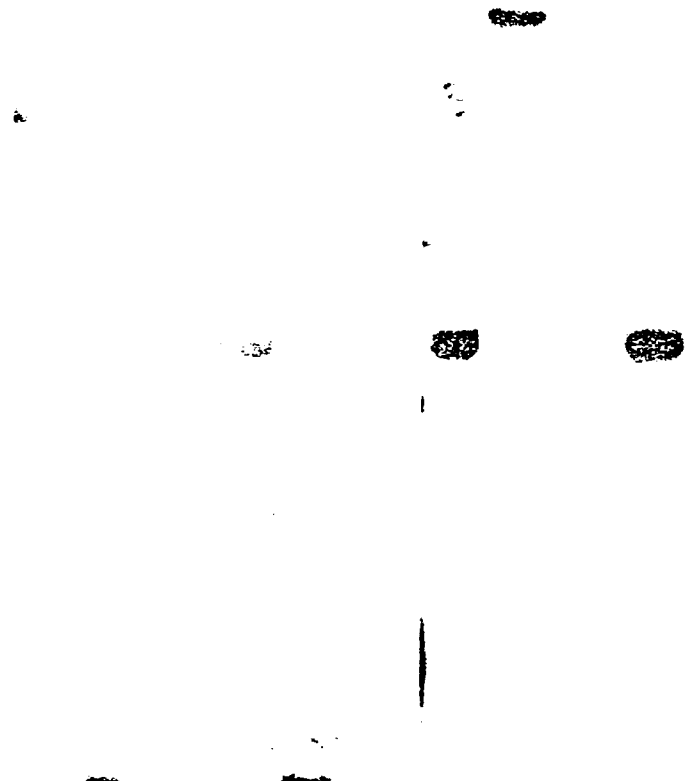

FIG. 7 shows the reactivity of the serum of four patients with HHV-6 epitopes.

The DNA sequences encoding the immunogenic proteins and parts thereof were identified in a genomic HHV-6 gene bank with mono- and polyspecific rabbit antisera against HHV-6 proteins.

Rabbits were immunized with whole HHV-6 infected HSB-2 cells. The obtained antiserum reacted with at least 7 viral proteins (FIG. 4). Antibodies against a 100 kda protein of HHV-6 were purified from this serum. For this purpose, entire viral protein was subjected to preparative SDS polyacrylamide electrophoresis. Viral protein with a molecular weight of 100 kda was transferred to nitrocellulose membranes and incubated with the diluted rabbit serum. Antibodies that were specifically bound on the nitrocellulose sheets were eluted with 100 mm glycin at pH 2.7. The obtained antibodies reacted specifically with an HHV-6 virion protein of about 100 kda (FIG. 4). Both serum preparations were used to screen the genomic library.

The construct of a genomic library DNA from cosmids containing the entire HHV-6 genome in overlapping fragments was sheared by sonication. After addition of EcoRI linkers, EcoRI digestions and size fractionation it was ligated into the commercially available vector lambda zapII (Stratagene Inc., La Jolla, USA). After in vitro packaging a gene bank of 3×10$^5$ independent recombinants was obtained. Positive clones were identified by immunological screening using the sera mentioned and a commercially available detection system ('Pico blue', Stratagene Inc., La Jolla, USA). The identified lambda clones were then subcloned into the Bluescript SK- vector by 'in vivo excision' following the supplier's instructions (Stratagene Inc.). Four clones that were especially reactive in Western blots (pMF101, pMF90 (SEQ ID NO:7), pMF94 (SEQ ID NO:5), pMF295) (SEQ ID NO:6) were chosen for further characterization. The inserts of these clones were sequenced by Sanger's chain termination method. Data were analyzed by the Genetics Computer Group (GCG, Madison, Wis., USA) sequence analysis package. The predicted amino acid sequences were used for homology searches with the computer program FASTA (Pearson & Lipman, 1988) in a library containing all of the published herpesvirus sequences. The clones pMF94 (SEQ ID NO:5) and pMF295 (SEQ ID NO:6) were found to contain parts of the published Major Capsid Protein gene of HHV-6 (FIG. 1) (Littler et al., 1990), while pMF90 (SEQ ID NO:7) contains part of an open reading frame homologous to UL44 of HCMV (FIG. 2). The corresponding HHV-6 gene has recently been identified using monoclonal antibodies against a phosphorylated HHV-6 protein of 41 kda (Chang and Balachandran, 1991). However, the epitope identified by Chang et al. is located after amino acid 227 of their sequence, while pMF90 (SEQ ID NO:7) covers amino acids 119–187 only. No homologous gene could be found for the predicted amino acid sequence of clone pMF101. The insert of pMF101 was used to locate the gene within the virus genome. By hybridization with 7 cosmid clones that encompass the entire HHV-6 genome (Neipel et al., 1991) it could be located within an 1.4 kb EcoRI fragment close to the left terminal repeat (FIG. 5). Further sequencing in this area revealed an open reading frame coding for a protein of 870 amino acids with a predicted molecular weight of 97 kda (termed p100 hereinafter).

Five fragments of p100, comprising almost the complete protein (pDF446-4 (SEQ ID NO:9), pDF446-3 (SEQ ID NO:10), pD2Hae (SEQ ID NO:11), pD2Hind (SEQ ID NO:12), pMF101R (SEQ ID NO:13)), were prokaryotically expressed as β-galacosidase fusion protein in the vector pROS (Ellinger et al). In Western blot assays only the carboxyterminal clones reacted with both rabbit human HHV-6 positive sera (FIG. 6, FIG. 7). Fusion protein expressed from pMF101R (SEQ ID NO:3) was used to purify antibodies from rabbit serum as described above. The antibodies were used to carry out Western blot analyses with HHV-6 infected and uninfected HSB-2 cells. A protein of 100 kda was detected in infected cells only. Of all expression clones investigated so far the carboxyterminal parts of p100 were most reliably recognized by human HHV-6 positive sera in Western blot analyses. Since it would be possible only with great technical elaboration to isolate virion proteins in the amounts necessary for diagnostic aids, the manner of preparation by gene manipulation according to the invention is especially advantageous. In Western blot analyses using HHV-6 infected cells a protein of 100 kda is recognized most reliably by human sera. It could not have been expected that prokaryotically expressed p100 or parts thereof are invariably recognized by human sera, as the homologous gene of HCMV codes for a much larger protein, and the immunogenic parts of the HHV-6 gene did not show any homology to HCMV pp150. It is also surprising that the prokaryotically expressed part of an phosphorylated HHV-6 protein homologous to HCMV UL44 (pMF90) (SEQ ID NO:7) is recognized by most HHV-6 positive human sera.

It is possible according to the invention to use p100 and/or the fragment of the UL44 homologue of HHV-6 (pMF90) (SEQ ID NO:7) and/or the phosphorylated HHV-6 protein of 41 kD, or immunogenic parts thereof, which have been prepared, in prokaryotic or eukaryotic cells, for example yeast cells, human or animal cells, as a reagent for detecting HHV-6 antibodies, for example in an ELISA assay.

EXAMPLE

A fragment of 182 bp from the carboxyterminal part of HHV-6 p100 (nucleotides 2960–3141 in FIGS. 3A–3E) was ligated in the expression vector pROS (Ellinger, S. et al., 1989). The clone is termed pMF101R (SEQ ID NO:13). The BamHI-HindIII fragments from plasmid pMF90 (SEQ ID NO:7), pMF94 (SEQ ID NO:5), and pMF295 (SEQ ID NO:6) were also ligated into pROS. They are termed pD2MF90, pD2MF94, and pD2MF295, respectively. Transformation of the resulting hybrid plasmid into *E. coli* JK50 was followed by isolation of clones whose plasmid DNA had the expected restriction pattern. After induction of the lac promoter with isopropyl-β-D-thiogalactopyranoside (IPTG) the clones expressed large amounts of a fusion protein having a viral fraction. The fusion proteins were isolated from the bacterial cells and used in Western blotting experiments. All human sera that were HHV-6 positive in a standard immunofluorescence assay using HHV-6 infected HSB-2 cells recognized at least one of the fusion proteins (FIG. 6). Human sera that were found to be HHV-6 negative using the immunofluorescence did react weakly or not at all.

Thus, prokaryotically expressed parts of p100 or the UL44 homologue of HHV-6 can be used in a diagnostic assay that is more sensitive and specific than the immunofluorescence used so far.

REFERENCES

Chang, C. K. and Balachandran, N. (1991) Identification, Characterization, and sequence Analysis of a cDNA Encoding a Phosphoprotein of Human Herpesvirus 6. J. Virol., 65:2884–2894.

Larcher, C., Huemer, H. P., Margreiter, R., and Dierich, M. P. (1988) Serological crossreaction of human herpesvirus-6 with cytomegalovirus [letter]. Lancet, 2:963–964.

Lawrence, G. L., Chee, M., Craxton, M. A., Gompels, U. A., Honess, R. W., and Barrell, B. G. (1990) Human herpesvirus 6 is closely related to human cytomegalovirus. J. Virol., 64:287–299.

Littler, E., Lawrence, G., Liu, M. Y., Barrell, B. G., and Arrand, J. R. (1990) Identification, cloning, and expression of the major capsid protein gene of human herpesvirus 6. J. Virol., 64:714–722.

Neipel, F., Ellinger, K., and Fleckenstein, B. (1991) The unique region of the human herpesvirus type 6 genome is essentially colinear to the UL segment of human cytomegalovirus. J. Gen. Virol., Yamamoto, M., Black, J. B., Stewart, J. A., Lopez, C., and Pellett, P. E. (1990) Identification of a nucleocapsid protein as a specific serological marker of human herpesvirus 6 infection. J. Clin. Microbiol., 28:1957–1962.

What is claimed is:

1. An isolated HHV-6 (human herpesvirus type 6) protein p100 having the amino acid sequence given in FIGS. 3A–3E, SEQ ID NO:1 or a part thereof, wherein said part thereof binds specifically to an antibody that specifically binds to the HHV-6 p100 protein comprising the amino acid sequence given in FIGS. 3A–3E, SEQ ID NO:1, and
   wherein said antibody does not bind to a component of human cytomegalovirus or other herpesviruses.

2. A composition comprising a protein according to claim 1 optionally in combination with a pharmaceutically acceptable carrier and/or diluent.

3. The composition according to claim 2 additionally containing parts of the major capsid protein of HHV-6 encoded by the DNA sequences given in FIG. 1 (SEQ ID NOS:5 and 6).

4. The composition according to claim 2 additionally containing parts of phosphorylated HHV-6 protein of 41 kD, encoded by the DNA sequence given in FIG. 2 (SEQ ID NO:7).

5. A method for the differential diagnosis of herpesvirus virus type 6 (HHV-6) infection, comprising:
   (a) contacting the composition according to claim 2 with a biological sample and
   (b) detecting the immunological complexes formed between HHV-6 p100 protein of the composition and antibodies in the biological sample, wherein the presence of immunological complexes is indicative of the presence of HHV-6 in the biological sample.

6. The method of claim 5, wherein said method comprises an ELISA.

* * * * *

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
      (A) LENGTH: 870 amino acids
      (B) TYPE: amino acid
      (D) TOPOLOGY: linear (ii) MOLECULE TYPE: protein (xi) SEQUENCE DESCRIPTION: SEQ ID NO:1:

```
Met Asp Leu Gln Arg His Pro Ile Pro Phe Ala Trp Leu Asp Arg Asp
1               5                   10                  15

Lys Val Glu Arg Leu Thr Asp Phe Leu Ser Asn Leu Glu Arg Leu Asp
                20                  25                  30

Asn Val Asp Leu Arg Glu His Pro His Val Thr Asn Ser Cys Val Val
            35                  40                  45

Arg Glu Gly Asp Asp Val Asp Asp Leu Lys Thr Leu Tyr Asn Leu Leu
    50                  55                  60

Val Leu Trp Leu Met Tyr His Tyr Val Leu Ser Lys Arg Lys Pro Asp
65                  70                  75                  80

Tyr Asn Ala Ile Trp Gln Asp Ile Thr Lys Leu Gln Ser Val Val Asn
                85                  90                  95

Glu Tyr Leu Asn Ser Lys Gly Leu Asn Lys Gly Ile Phe Glu Asn Met
                100                 105                 110

Phe Thr Asn Lys Glu Lys Phe Glu Ser Gln Phe Ser Asp Ile Asn Arg
            115                 120                 125

Ala Leu Leu Arg Leu Gly Asn Phe Ile Lys Trp Gly Ser Asn Val Ala
        130                 135                 140
```

```
Ile Asp Thr Pro Tyr Val Asn Leu Thr Ala Glu Asp Ser Ser Glu Ile
145                 150                 155                 160

Glu Asn Asn Leu Gln Asp Ala Glu Lys Asn Met Leu Trp Tyr Thr Val
            165                 170                 175

Tyr Asn Ile Asn Asp Pro Trp Asp Glu Asn Gly Tyr Leu Ile Thr Ser
            180                 185                 190

Ile Asn Lys Leu Ile Tyr Leu Gly Lys Leu Phe Leu Ala Leu Thr Gln
            195                 200                 205

Ser Trp Ser Lys Leu Glu Lys Val Ala Met Ser Gln Ile Val Ile Thr
    210                 215                 220

Gln Asn His Leu Ser Gly His Leu Arg Arg His Asp Asn Phe Asn Ile
225                 230                 235                 240

Val Tyr Ser His Arg Val Leu Gln Thr Pro Leu Thr Gly Gln Arg Val
            245                 250                 255

Glu Ser Phe Leu Lys Ile Ile Thr Ser Asp Tyr Asp Ile Ile Lys Ser
            260                 265                 270

Ser Leu Glu Ser His Ser Ala Ser Lys Ala Phe Ser Met Ser Glu Ile
    275                 280                 285

Gly Pro Asn Ser Leu Met Asp Phe Val Pro Leu Arg Gly Asp Ile His
    290                 295                 300

Ser Asn Leu Thr Leu Pro Ser Met Ser Ile Asp Thr Lys Lys Ser Ser
305                 310                 315                 320

Leu Asp Pro Ala Arg Leu Lys Lys Ser Asn Ser Arg Ser Leu Asp Ser
                325                 330                 335

Phe Leu Arg Met Gln Arg Gln Pro Lys Phe Leu Glu Leu Asp Ser Val
            340                 345                 350

Asp Asn Ala Gly Glu Lys Ile Leu Leu Lys Glu Ala Thr Leu Gly Gly
            355                 360                 365

Glu Asn Val Lys Ala Thr Thr Pro Ala Ser Ser Val Ser Leu Met Ser
    370                 375                 380

Gly Val Glu Ser Pro Ser Ser Phe Thr Ser Thr Asn Leu Asp Leu Pro
385                 390                 395                 400

Leu Ser Ser Phe Thr Ser Thr Asn Leu Asp Leu Arg Asp Lys Ser His
            405                 410                 415

Gly Asn Tyr Lys Ile Gly Pro Ser Gly Ile Leu Asp Phe Asn Val Lys
            420                 425                 430

Phe Pro Pro Asn Ala Gln Leu Asn Thr Asn Gly Val Asp Leu Leu Gln
            435                 440                 445

Asp Lys Thr Ser Ile Gly Ser Pro Ser Ser Gly Ile Thr Asp Val Val
    450                 455                 460

Asn Gly Phe Ala Asn Leu Asn Leu His Gln Asn Lys Ser Asn Val Ser
465                 470                 475                 480

Pro Pro Trp Ser Arg Asn Thr Ala Ala Asn Ala Asp Phe Leu Asp Pro
            485                 490                 495

Val His Arg Phe Val Pro Glu Gln Thr Gly Thr Pro Phe Val Leu Asn
            500                 505                 510

Asn Ser Asp Val Ala Gly Ser Glu Ala Lys His Thr Thr Tyr Ser Thr
            515                 520                 525

Glu Thr Gly Val Ser Pro Arg Asn Val Phe Leu Ile Lys Asp Leu Arg
    530                 535                 540

Gly Lys Asp Gly Phe Arg Lys Gln Lys Gln Ser Asp Ile Pro Lys Ser
545                 550                 555                 560
```

-continued

```
Leu Thr Lys Glu Arg Asn Asp Lys Ala Ile Met His Ser Arg Glu Val
            565                 570                 575
Thr Gly Asp Ser Gly Asp Ala Thr Glu Thr Val Gly Ala Arg Asn Ser
            580                 585                 590
Pro Ala Leu Arg Lys Ile Lys Gln Ala Asn Asp Phe Phe Ala Gly Leu
            595                 600                 605
Asn Lys Lys Asn Asp Arg Asp Val Leu Arg Gly Lys Gly Asn Ser
610                 615                 620
Lys Asp Leu His Ser Gly Gly Asn Ala Lys Lys Glu Met Ser Gly
625                 630                 635                 640
Lys Phe Asn Asp Asp Lys Glu Met Thr Arg Asn Gly Gln Glu Pro Ser
            645                 650                 655
Arg Ser Leu Met Gly Asp Ala Arg Asn Ala Gly Asp Glu Gln Tyr Ile
            660                 665                 670
Gln Ala Gly Leu Gly Gln Arg Val Asn Asn Leu Leu Ser Gln Phe Thr
            675                 680                 685
Asn Leu Ile Ser Leu Gly Glu Lys Gly Ile Glu Asp Ile Leu Gln Asn
            690                 695                 700
Gln Arg Gly Thr Glu Leu Lys Leu Ala Thr Glu Asn Lys Ser Gly Arg
705                 710                 715                 720
Glu Ser Glu Glu Ala Asn Val Glu Lys Ile Leu Glu Val Ser Asn Pro
            725                 730                 735
Gln Asp Met Phe Lys Asn Phe Arg Leu Gln Asn Asp Leu Asp Ser Val
            740                 745                 750
Gln Ser Pro Phe Arg Leu Pro Asp Ala Asp Leu Ser Arg Glu Leu Asp
            755                 760                 765
Ser Ala Ser Phe Lys Asp Ala Leu Asp Leu Lys Leu Pro Gly Asn Gly
            770                 775                 780
Glu Arg Glu Ile Asp Leu Ala Leu Glu Lys Val Lys Val Gly Glu Thr
785                 790                 795                 800
Glu Thr Ser Asp Leu Lys Val Gly Gln Asp Glu Ser Phe Val Pro Ala
            805                 810                 815
Gln Leu Met Lys Val Glu Thr Pro Glu Glu Lys Asp Asp Ile Ile Glu
            820                 825                 830
Gln Met Val Leu Arg Ile Arg Gln Asp Gly Glu Thr Asp Glu Asn Thr
            835                 840                 845
Val Ser Gly Pro Gly Val Ala Glu Ser Leu Asp Ile Glu Ala Lys Gly
            850                 855                 860
Glu Ser Ala Ile Ala Ser
865                 870
```

(2) INFORMATION FOR SEQ ID NO:2:

(i) SEQUENCE CHARACTERISTICS:
        (A) LENGTH: 2610 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

```
ATGGATCTGC AAAGACATCC GATTCCGTTT GCGTGGCTAG ATCGAGACAA AGTTGAGCGT      60

CTTACAGATT TTCTCAGCAA TTTGGAAAGA CTGGATAATG TAGATTTGCG AGAGCATCCC     120

CATGTGACTA ATTCTTGTGT CGTGAGAGAG GGAGACGATG TAGACGATTT AAAAACATTG     180
```

-continued

| | | | | | |
|---|---|---|---|---|---|
| TATAACCTAC | TAGTGTTATG | GCTTATGTAT | CACTACGTCT | TATCTAAAAG | GAAGCCGGAT | 240 |
| TATAATGCTA | TATGGCAAGA | CATCACGAAA | CTCCAAAGTG | TCGTAAACGA | GTACTTAAAC | 300 |
| TCCAAAGGTC | TGAATAAAGG | AATTTTTGAA | AATATGTTCA | CGAACAAAGA | AAAGTTTGAA | 360 |
| TCGCAATTCA | GTGATATTAA | TCGCGCTTTA | CTGCGTTTAG | GAAACTTTAT | TAAGTGGGGT | 420 |
| AGCAATGTTG | CGATCGATAC | TCCTTATGTA | AATCTTACTG | CAGAAGACAG | CAGCGAGATA | 480 |
| GAAAATAATT | TGCAAGATGC | TGAAAAAAAC | ATGCTGTGGT | ATACCGTCTA | TAACATAAAT | 540 |
| GACCCCTGGG | ACGAAAACGG | TTACTTAATA | ACGAGTATTA | ATAAATTAAT | TTATCTCGGT | 600 |
| AAGTTATTTT | TAGCGTTAAC | TCAGTCCTGG | TCAAAGCTAG | AAAAGGTTGC | TATGAGTCAA | 660 |
| ATTGTAATCA | CGCAAAATCA | TCTCTCGGGT | CATTTGAGGA | GGCACGACAA | TTTTAATATT | 720 |
| GTATATTCTC | ATAGGGTTTT | GCAGACTCCT | CTGACTGGTC | AAAGAGTAGA | GAGTTTTCTG | 780 |
| AAAATAATCA | CCAGTGATTA | TGATATTATC | AAAAGTAGTC | TGGAATCACA | CAGCGCGTCG | 840 |
| AAAGCATTTT | CGATGTCTGA | GATTGGGCCT | AATTCTTTAA | TGGATTTCGT | CCCTTTACGC | 900 |
| GGCGATATAC | ATTCAAATTT | GACTTTACCT | AGTATGTCTA | TAGATACAAA | GAAATCATCT | 960 |
| TTAGATCCGG | CTCGTCTGAA | AAAAGTAAT | TCCAGAAGTT | TGGATAGTTT | CTTAAGAATG | 1020 |
| CAGAGACAAC | CTAAATTTCT | AGAGTTGGAT | AGCGTTGATA | ATGCCGGGGA | AAAAATTTTA | 1080 |
| CTAAAGGAAG | CAACACTCGG | GGGTGAAAAC | GTTAAAGCGA | CAACGCCTGC | TTCCTCTGTC | 1140 |
| TCTTTAATGT | CCGGAGTTGA | GTCGCCGTCG | TCTTTCACTT | CTACCAATCT | GGATCTGCCG | 1200 |
| TTGTCGTCTT | TCACTTCTAC | TAATCTGGAT | CTGCGAGATA | AGTCGCACGG | TAATTATAAA | 1260 |
| ATTGGCCCTT | CGGGGATTTT | AGATTTTAAT | GTTAAATTTC | CACCTAATGC | GCAATTGAAT | 1320 |
| ACGAACGGTG | TGGATTTACT | ACAGGATAAA | ACTTCGATCG | GGAGTCCCAG | TAGCGGTATT | 1380 |
| ACCGATGTGG | TAAATGGTTT | CGCTAATCTC | AATCTGCATC | AGAATAAATC | AAATGTTTCG | 1440 |
| CCACCGTGGA | GCAGAAACAC | AGCGGCGAAT | GCGGACTTTT | TAGATCCGGT | GCATCGCTTT | 1500 |
| GTTCCTGAGC | AGACAGGGAC | ACCCTTCGTG | TTGAATAATT | CCGACGTGGC | GGGATCAGAA | 1560 |
| GCGAAGCATA | CGACTTACAG | TACGGAGACC | GGCGTTTCAC | CCCGTAACGT | TTTTCTCATT | 1620 |
| AAAGATTTGA | GAGGCAAAGA | CGGTTTTAGG | AAACAGAAGC | AGTCAGATAT | TCCGAAAAGC | 1680 |
| TTAACTAAGG | AAAGAAATGA | TAAAGCTATA | ATGCACTCAC | GCGAGGTGAC | CGGAGATTCT | 1740 |
| GGCGATGCGA | CTGAAACTGT | GGGTGCTCGG | AATTCCCCGG | CGTTGAGAAA | AATTAAGCAA | 1800 |
| GCAAATGATT | TTTTTGCCGG | GTTAAATAAG | AAAAATGATC | GTGACGTATT | AAGAGGGGGG | 1860 |
| AAAGGAAATA | GCAAGGACTT | GCATTCTGGC | GGCAATGCAA | AAAAAAAGA | AATGTCGGGA | 1920 |
| AAGTTTAATG | ACGATAAAGA | AATGACGCGA | AACGGACAAG | AGCCATCACG | TAGTTTAATG | 1980 |
| GGAGATGCTA | GAAATGCCGG | AGATGAACAA | TATATTCAAG | CGGGTCTCGG | GCAGCGAGTT | 2040 |
| AACAATCTTC | TAAGTCAATT | TACAAATCTG | ATTAGTTTAG | GCGAGAAGGG | CATCGAAGAC | 2100 |
| ATTTTGCAGA | ATCAGCGCGG | GACCGAGTTA | AAGTTGGCTA | CAGAAAACAA | GTCGGGACGC | 2160 |
| GAATCGGAGG | AAGCTAACGT | AGAAAAAATT | CTTGAAGTTA | GTAATCCTCA | AGATATGTTT | 2220 |
| AAAAATTTTA | GGTTGCAAAA | CGATCTCGAT | TCCGTTCAGT | CTCCGTTTAG | GCTACCGGAT | 2280 |
| GCTGATTTGT | CTCGCGAGTT | AGATTCCGCG | TCATTTAAGG | ACGCGTTAGA | CTTGAAGCTT | 2340 |
| CCGGGTAACG | GAGAACGAGA | AATAGATCTC | GCTCTTGAAA | AAGTGAAGGT | AGGCGAGACG | 2400 |
| GAAACCTCAG | ATTTAAAAGT | CGGTCAGGAT | GAAAGTTTTG | TTCCTGCGCA | ATTAATGAAG | 2460 |
| GTTGAGACAC | CTGAAGAAAA | AGATGATATA | ATTGAACAGA | TGGTTCTGAG | GATACGTCAA | 2520 |
| GACGGGGAAA | CTGATGAAAA | CACCGTCTCT | GGGCCGGGAG | TCGCTGAGTC | TTTGGATATA | 2580 |

```
GAAGCCAAAG GCGAGTCAGC GATCGCGTCG                                           2610
```

(2) INFORMATION FOR SEQ ID NO:3:

(i) SEQUENCE CHARACTERISTICS:
        (A) LENGTH: 61 amino acids
        (B) TYPE: amino acid
        (D) TOPOLOGY: linear (ii) MOLECULE TYPE: protein (xi) SEQUENCE DESCRIPTION: SEQ ID NO:3:

```
Ala Leu Asp Leu Lys Leu Pro Gly Asn Gly Glu Arg Glu Ile Asp Leu
 1               5                  10                  15

Ala Leu Glu Lys Val Lys Val Gly Glu Thr Glu Thr Ser Asp Leu Lys
            20                  25                  30

Val Gly Gln Asp Glu Ser Phe Val Pro Ala Gln Leu Met Lys Val Glu
        35                  40                  45

Thr Pro Glu Glu Lys Asp Asp Ile Ile Glu Gln Met Val
    50                  55                  60
```

(2) INFORMATION FOR SEQ ID NO:4:

(i) SEQUENCE CHARACTERISTICS:
        (A) LENGTH: 552 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

```
GAATTCCCCG GCGTTGAGAA AAATTAAGCA AGCAAATGAT TTTTTTGCCG GGTTAAATAA    60
GAAAAATGAT CGTGACGTAT TAAGAGGGGG GAAAGGAAAT AGCAAGGACT TGCATTCTGG   120
CGGCAATGCA AAAAAAAAAG AAATGTCGGG AAAGTTTAAT GACGATAAAG AAATGACGCG   180
AAACGGACAA GAGCCATCAC GTAGTTTAAT GGGAGATGCT AGAAATGCCG GAGATGAACA   240
ATATATTCAA GCGGGTCTCG GCAGCGAGT  TAACAATCTT CTAAGTCAAT TTACAAATCT   300
GATTAGTTTA GGCGAGAAGG GCATCGAAGA CATTTTGCAG AATCAGCGCG GGACCGAGTT   360
AAAGTTGGCT ACAGAAAACA AGTCGGGACG CGAATCGGAG GAAGCTAACG TAGAAAAAAT   420
TCTTGAAGTT AGTAATCCTC AAGATATGTT TAAAAATTTT AGGTTGCAAA ACGATCTCGA   480
TTCCGTTCAG TCTCCGTTTA GGCTACCGGA TGCTGATTTG TCTCGCGAGT TAGATTCCGC   540
GTCATTTAAG GA                                                      552
```

(2) INFORMATION FOR SEQ ID NO:5:

(i) SEQUENCE CHARACTERISTICS:
        (A) LENGTH: 441 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

```
GAATTCCTGA CGCCAGCGCC ACAGGCCTTG TTATTTGATA GTGCCGGGAG TACGCAGAAG    60
TAAAATATCT TGCTCAGGAT GGTGGTTTCG TTCGATGGTC TGTCATTGTC GGTAAAGACG   120
ACGCTTGAAT CTATTAGATT CATTCTTTGC ACATCGGATA TTTCGTAATT TCTAACTCTT   180
```

```
ACGGTGTTCT GTGTCAGTGG TGTATCATCC GCTGTTATTT TTGCATTCGT GTCGTTTCTG      240

GGCATGGTAT GGACGAACGG GCAGAACAGA CGTCCGTCGA CAACGCGTT GGCGAAATTC       300

ACCAGAGGTT CGCCGCAAAG TTGCTCGTTG AGGTTGGAGA TAGAGATTGT TCTCTTCACT      360

AGGCGAATTA GCGACACAAG ATTTCTGTAG TGAGCGAAAG CTGCTCCCGG GATCAGTTCG      420

TCGCCCATGT GGTTGGAATT C                                                441
```

(2) INFORMATION FOR SEQ ID NO:6:

(i) SEQUENCE CHARACTERISTICS:
        (A) LENGTH: 219 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

```
CCGTGTGAAA TTAAACGACA CCATGGAAAA CAACCTACCC ACCAGCGTTT TTTTCCACAA       60

TAAAGACCAA GTCGTGCAGC GAATTGATTT TGCCGACATA TTACCGTCGG TTTGCCATCC      120

CATTGTCCAC GACTCGACCA TCGTCGAACG ACTCATGAAA AGCGAACCAT TGCCTACCGG      180

CCACCGCTTT TCCCAACTAT GTCAACTAAA AATTACCCG                             219
```

(2) INFORMATION FOR SEQ ID NO:7:

(i) SEQUENCE CHARACTERISTICS:
        (A) LENGTH: 205 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

```
CCACTTTTTG AAAGTTTTAT GAACATCATC TCGAATCCTG AGGTTACGAA GATGTACATT       60

CAGCATGATA GTGATCTGTA TACGAGGGTT TTGGTAACGG CTTCCGATAC ATGTACACAG      120

GCGTCGGTTC CCTGTGTGCA CGGACAAGAA GTGGTGCGAG ACACCGGGAG ATCGCCGTTG      180

AGGATTGACC TTGATCATTC GACCG                                            205
```

(2) INFORMATION FOR SEQ ID NO:8:

(i) SEQUENCE CHARACTERISTICS:
        (A) LENGTH: 3868 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: modified_base
        (B) LOCATION: 14
        (D) OTHER INFORMATION: /mod_base= OTHER
            /note= "N is unknown."

(ix) FEATURE:
        (A) NAME/KEY: modified_base
        (B) LOCATION: 3695
        (D) OTHER INFORMATION: /mod_base= OTHER
            /note= "N is unknown."

(xi) SEQUENCE DESCRIPTION: SEQ ID NO:8:

```
GAATTCCTAT GTTNCGCCCC GTGCTAGATG TTTTACTTTC AGTCTTTTTA CGCCGGTGTA       60
```

-continued

```
AGGTTTTGTA CCTGATAGTT GCGATTATAG CTAGCATGCT TATACTATAT GAACAGACTG    120

CATGATAGAT GAAGTAAACT AACTGACAGA AAAAACGGTT GAATGAGAAC AGTTGCTTTC    180

TGTTCACTGT CATAAAAAAG ACACACCACA TGAGCACAAA ATCGCTAGCA AAGAGTGTGA    240

TGACGTAAAA TGAAGTAGCG TTATGTTTTG CGACTCTGTG GTAGAGAATC ATGGTGGTAA    300

CCACTATAAT GATCATGGGG ATAGATGTGG TGAGCGTGAT TCCGGTAACT GCGCTCTCCA    360

TGATTCGTGC TGTCTTTAGC GTGGGTGTCG AGGTACAGGA AGCATTGCCT TTGAACTCTT    420

CATTGCGCTA TTAAAGATAT TGAATGTTAT TTTCATGTTA CGCTACATTA AAATATTCGG    480

TAACAATGAT GTCTGAAGAC TTACCAGAAG TTTGGACAGC TCAATGACAG TGTCCATCTC    540

GTCGCTTGTC AGTTTTCTGT GTGGGTAAAA AAAGACTATA TAAACATTGA ATGTTGGCGG    600

AAATGAGCAG TTCTGTTTTT GAGTTTGTTT TCTAAAATAT GGATCTGCAA AGACATCCGA    660

TTCCGTTTGC GTGGCTAGAT CGAGACAAAG TTGAGCGTCT TACAGATTTT CTCAGCAATT    720

TGGAAAGACT GGATAATGTA GATTTGCGAG AGCATCCCCA TGTGACTAAT TCTTGTGTCG    780

TGAGAGAGGG AGACGATGTA GACGATTTAA AAACATTGTA TAACCTACTA GTGTTATGGC    840

TTATGTATCA CTACGTCTTA TCTAAAAGGA AGCCGGATTA TAATGCTATA TGGCAAGACA    900

TCACGAAACT CCAAAGTGTC GTAAACGAGT ACTTAAACTC CAAAGGTCTG AATAAAGGAA    960

TTTTTGAAAA TATGTTCACG AACAAAGAAA AGTTTGAATC GCAATTCAGT GATATTAATC   1020

GCGCTTTACT GCGTTTAGGA AACTTTATTA AGTGGGGTAG CAATGTTGCG ATCGATACTC   1080

CTTATGTAAA TCTTACTGCA GAAGACAGCA GCGAGATAGA AAATAATTTG CAAGATGCTG   1140

AAAAAAACAT GCTGTGGTAT ACCGTCTATA ACATAAATGA CCCCTGGGAC GAAAACGGTT   1200

ACTTAATAAC GAGTATTAAT AAATTAATTT ATCTCGGTAA GTTATTTTTA GCGTTAACTC   1260

AGTCCTGGTC AAAGCTAGAA AAGGTTGCTA TGAGTCAAAT TGTAATCACG CAAAATCATC   1320

TCTCGGGTCA TTTGAGGAGG CACGACAATT TTAAATATTG ATATTCTCAT AGGGTTTTGC   1380

AGACTCCTCT GACTGGTCAA AGAGTAGAGA GTTTTCTGAA ATAATCACC AGTGATTATG    1440

ATATTATCAA AAGTAGTCTG GAATCACACA GCGCGTCGAA AGCATTTTCG ATGTCTGAGA   1500

TTGGGCCTAA TTCTTTAATG GATTTCGTCC CTTTACGCGG CGATATACAT TCAAATTTGA   1560

CTTTACCTAG TATGTCTATA GATACAAAGA AATCATCTTT AGATCCGGCT CGTCTGAAAA   1620

AAAGTAATTC CAGAAGTTTG GATAGTTTCT TAAGAATGCA GAGACAACCT AAATTTCTAG   1680

AGTTGGATAG CGTTGATAAT GCCGGGGAAA AAATTTACT AAAGGAAGCA ACACTCGGGG    1740

GTGAAAACGT TAAAGCGACA ACGCCTGCTT CCTCTGTCTC TTTAATGTCC GGAGTTGAGT   1800

CGCCGTCGTC TTTCACTTCT ACCAATCTGG ATCTGCCGTT GTCGTCTTTC ACTTCTACTA   1860

ATCTGGATCT GCGAGATAAG TCGCACGGTA ATTATAAAAT TGGCCCTTCG GGGATTTTAG   1920

ATTTTAATGT TAAATTTCCA CCTAATGCGC AATTGAATAC GAACGGTGTG GATTTACTAC   1980

AGGATAAAAC TTCGATCGGG AGTCCCAGTA GCGGTATTAC CGATGTGGTA AATGGTTTCG   2040

CTAATCTCAA TCTGCATCAG AATAAATCAA ATGTTTCGCC ACCGTGGAGC AGAAACACAG   2100

CGGCGAATGC GGACTTTTTA GATCCGGTGC ATCGCTTTGT TCCTGAGCAG ACAGGGACAC   2160

CCTTCGTGTT GAATAATTCC GACGTGGCGG GATCAGAAGC GAAGCATACG ACTTACAGTA   2220

CGGAGACCGG CGTTTCACCC CGTAACGTTT TTCTCATTAA AGATTTGAGA GGCAAAGACG   2280

GTTTTAGGAA ACAGAAGCAG TCAGATATTC CGAAAAGCTT AACTAAGGAA AGAAATGATA   2340

AAGCTATAAT GCACTCACGC GAGGTGACCG GAGATTCTGG CGATGCGACT GAAACTGTGG   2400

GTGCTCGGAA TTCCCCGGCG TTGAGAAAAA TTAAGCAAGC AAATGATTTT TTTGCCGGGT   2460
```

-continued

```
TAAATAAGAA AAATGATCGT GACGTATTAA GAGGGGGGAA AGGAAATAGC AAGGACTTGC      2520

ATTCTGGCGG CAATGCAAAA AAAAAAGAAA TGTCGGGAAA GTTTAATGAC GATAAAGAAA      2580

TGACGCGAAA CGGACAAGAG CCATCACGTA GTTTAATGGG AGATGCTAGA AATGCCGGAG      2640

ATGAACAATA TATTCAAGCG GGTCTCGGGC AGCGAGTTAA CAATCTTCTA AGTCAATTTA      2700

CAAATCTGAT TAGTTTAGGC GAGAAGGGCA TCGAAGACAT TTTGCAGAAT CAGCGCGGGA      2760

CCGAGTTAAA GTTGGCTACA GAAAACAAGT CGGGACGCGA ATCGGAGGAA GCTAACGTAG      2820

AAAAAATTCT TGAAGTTAGT AATCCTCAAG ATATGTTTAA AAATTTTAGG TTGCAAAACG      2880

ATCTCGATTC CGTTCAGTCT CCGTTTAGGC TACCGGATGC TGATTTGTCT CGCGAGTTAG      2940

ATTCCGCGTC ATTTAAGGAC GCGTTAGACT TGAAGCTTCC GGGTAACGGA GAACGAGAAA      3000

TAGATCTCGC TCTTGAAAAA GTGAAGGTAG GCGAGACGGA AACCTCAGAT TTAAAAGTCG      3060

GTCAGGATGA AAGTTTTGTT CCTGCGCAAT TAATGAAGGT TGAGACACCT GAAGAAAAAG      3120

ATGATATAAT TGAACAGATG GTTCTGAGGA TACGTCAAGA CGGGGAAACT GATGAAAACA      3180

CCGTCTCTGG GCCGGGAGTC GCTGAGTCTT TGGATATAGA AGCCAAAGGC GAGTCAGCGA      3240

TCGCGTCGTG ATGTAAAAAA TTTTCTCTGG GGAGTTTCAG GTTGCCAATA AAATGCCCAT      3300

TCTCAGACAG CTTTGCGATT ACGTCTTTTT GTTCATTGTT CTGGCTTGTC ATTCTTTCTA      3360

CATAAAACAG GGTCGCGATA GGTGTGCTTT GAGGCAGGAT CAGATTTGGA GAAAATGAAC      3420

GCAGCGTAAT GTGCAAAGGT GTTCCCGGGG CCCACAGCAT CACCTGGGTT TCGAAGAATC      3480

CTTCGTTCTG GTAGCCGGAT ATGAGGATTT GCTTGTCGGG CTTTGTGAAA TATCGGATAG      3540

GTAGAATTAC TATGTGGCAT CGGCTTGGAT AGAAATGGAT GTCATATGGT GCGTGTACAA      3600

GTAGCTCGTA ATAATTTGGG TTGTGTTGCA GTTGTATCGT TGCGTTTAGT ACGTCTCCTG      3660

TAAAATATAA TTTCGGGTTA CTGGAAAATA ACAGNGGTTC GGGCTCTTCG ATTTGCGTTA      3720

CCACTTCAAA CTGAACTATT AAATATTTCG GTAGATTTTC CGTTGTTAGT AAAGAAGGGA      3780

TTTGCTCGCA GCATACAGTG GCTAGTGTTC CAAAAACTTT TTCTTTGTTT TTGACGAGAC      3840

CGAGATTTTC AATGTTAATC GAGAATTC                                        3868
```

(2) INFORMATION FOR SEQ ID NO:9:

(i) SEQUENCE CHARACTERISTICS:
        (A) LENGTH: 697 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

```
TAAAAACATT GTATAACCTA CTAGTGTTAT GGCTTATGTA TCACTACGTC TTATCTAAAA       60

GGAAGCCGGA TTATAATGCT ATATGGCAAG ACATCACGAA ACTCCAAAGT GTCGTAAACG      120

AGTACTTAAA CTCCAAAGGT CTGAATAAAG GAATTTTTGA AAATATGTTC ACGAACAAAG      180

AAAAGTTTGA ATCGCAATTC AGTGATATTA ATCGCGCTTT ACTGCGTTTA GGAAACTTTA      240

TTAAGTGGGG TAGCAATGTT GCGATCGATA CTCCTTATGT AAATCTTACT GCAGAAGACA      300

GCAGCGAGAT AGAAAATAAT TTGCAAGATG CTGAAAAAAA CATGCTGTGG TATACCGTCT      360

ATAACATAAA TGACCCCTGG GACGAAAACG GTTACTTAAT AACGAGTATT AATAAATTAA      420

TTTATCTCGG TAAGTTATTT TTAGCGTTAA CTCAGTCCTG GTCAAAGCTA GAAAAGGTTG      480

CTATGAGTCA AATTGTAATC ACGCAAAATC ATCTCTCGGG TCATTTGAGG AGGCACGACA      540
```

```
ATTTTAATAT TGTATATTCT CATAGGGTTT TGCAGACTCC TCTGACTGGT CAAAGAGTAG      600

AGAGTTTTCT GAAAATAATC ACCAGTGATT ATGATATTAT CAAAAGTAGT CTGGAATCAC      660

ACAGCGCGTC GAAAGCATTT TCGATGTCTG AGATTGG                               697
```

(2) INFORMATION FOR SEQ ID NO:10:

(i) SEQUENCE CHARACTERISTICS:
        (A) LENGTH: 505 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

```
GCCCTTCGGG GATTTTAGAT TTTAATGTTA AATTTCCACC TAATGCGCAA TTGAATACGA       60

ACGGTGTGGA TTTACTACAG GATAAAACTT CGATCGGGAG TCCCAGTAGC GGTATTACCG      120

ATGTGGTAAA TGGTTTCGCT AATCTCAATC TGCATCAGAA TAAATCAAAT GTTTCGCCAC      180

CGTGGAGCAG AAACACAGCG GCGAATGCGG ACTTTTTAGA TCCGGTGCAT CGCTTTGTTC      240

CTGAGCAGAC AGGGACACCC TTCGTGTTGA ATAATTCCGA CGTGGCGGGA TCAGAAGCGA      300

AGCATACGAC TTACAGTACG GAGACCGGCG TTTCACCCCG TAACGTTTTT CTCATTAAAG      360

ATTTGAGAGG CAAAGACGGT TTTAGGAAAC AGAAGCAGTC AGATATTCCG AAAAGCTTAA      420

CTAAGGAAAG AAATGATAAA GCTATAATGC ACTCACGCGA GGTGACCGGA GATTCTGGCG      480

ATGCGACTGA AACTGTGGGT GCTCG                                           505
```

(2) INFORMATION FOR SEQ ID NO:11:

(i) SEQUENCE CHARACTERISTICS:
        (A) LENGTH: 399 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

```
GCCTAATTCT TTAATGGATT TCGTCCCTTT ACGCGGCGAT ATACATTCAA ATTTGACTTT       60

ACCTAGTATG TCTATAGATA CAAAGAAATC ATCTTTAGAT CCGGCTCGTC TGAAAAAAAG      120

TAATTCCAGA AGTTTGGATA GTTTCTTAAG AATGCAGAGA CAACCTAAAT TTCTAGAGTT      180

GGATAGCGTT GATAATGCCG GGGAAAAAAT TTTACTAAAG GAAGCAACAC TCGGGGGTGA      240

AAACGTTAAA GCGACAACGC CTGCTTCCTC TGTCTCTTTA ATGTCCGGAG TTGAGTCGCC      300

GTCGTCTTTC ACTTCTACCA ATCTGGATCT GCCGTTGTCG TCTTTCACTT CTACTAATCT      360

GGATCTGCGA GATAAGTCGC ACGGTAATTA TAAAATTGG                             399
```

(2) INFORMATION FOR SEQ ID NO:12:

(i) SEQUENCE CHARACTERISTICS:
        (A) LENGTH: 566 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

```
GAATTCCCCG GCGTTGAGAA AAATTAAGCA AGCAAATGAT TTTTTTGCCG GGTTAAATAA       60
```

```
GAAAAATGAT CGTGACGTAT TAAGAGGGGG GAAAGGAAAT AGCAAGGACT TGCATTCTGG      120

CGGCAATGCA AAAAAAAAAG AAATGTCGGG AAAGTTTAAT GACGATAAAG AAATGACGCG      180

AAACGGACAA GAGCCATCAC GTAGTTTAAT GGGAGATGCT AGAAATGCCG GAGATGAACA      240

ATATATTCAA GCGGGTCTCG GGCAGCGAGT TAACAATCTT CTAAGTCAAT TTACAAATCT      300

GATTAGTTTA GGCGAGAAGG GCATCGAAGA CATTTTGCAG AATCAGCGCG GGACCGAGTT      360

AAAGTTGGCT ACAGAAAACA AGTCGGGACG CGAATCGGAG GAAGCTAACG TAGAAAAAAT      420

TCTTGAAGTT AGTAATCCTC AAGATATGTT TAAAAATTTT AGGTTGCAAA ACGATCTCGA      480

TTCCGTTCAG TCTCCGTTTA GGCTACCGGA TGCTGATTTG TCTCGCGAGT TAGATTCCGC      540

GTCATTTAAG GACGCGTTAG ACTTGA                                           566

(2) INFORMATION FOR SEQ ID NO:13:

(i) SEQUENCE CHARACTERISTICS:
        (A) LENGTH: 182 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

CGCGTTAGAC TTGAAGCTTC CGGGTAACGG AGAACGAGAA ATAGATCTCG CTCTTGAAAA       60

AGTGAAGGTA GGCGAGACGG AAACCTCAGA TTTAAAAGTC GGTCAGGATG AAAGTTTTGT      120

TCCTGCGCAA TTAATGAAGG TTGAGACACC TGAAGAAAAA GATGATATAA TTGAACAGAT      180

GG                                                                    182
```